United States Patent [19]
Stroefer et al.

[11] Patent Number: 4,788,293
[45] Date of Patent: Nov. 29, 1988

[54] PREPARATION OF 1-PYRAZOLINES

[75] Inventors: Eckhard Stroefer, Mannheim; Wolfgang Rohr, Wachenheim; Gerhard W. Rotermund, Mannheim; Rolf Fischer, Heidelberg; Reinhard Neudert, Bissersheim, all of Fed. Rep. of Germany

[73] Assignee: BASF Aktiengesellschaft, Fed. Rep. of Germany

[21] Appl. No.: 886,407

[22] Filed: Jul. 15, 1986

[30] Foreign Application Priority Data

Jul. 16, 1985 [DE] Fed. Rep. of Germany ....... 3525268

[51] Int. Cl.$^4$ ........................................... C07D 231/06
[52] U.S. Cl. ..................... 548/356; 548/369
[58] Field of Search ................................ 548/356, 369

[56] References Cited
FOREIGN PATENT DOCUMENTS
0162247 11/1985 European Pat. Off. ............ 548/373

OTHER PUBLICATIONS
A. F. Holleman, E. Wiberg, "Lehrbuch Der Anorganischen Chemie" Walter De Gruyter & Co., Berlin 1971, 80th ed., p. 349.
L. C. Behr et al., "Pyrazoles, Pyrazolines, Pyrazolidines, Indazoles and Condensed Rings," The Chem. of Heterocycl. Compounds, Interscience Publications, NY, 177–208 (1967).
R. J. Crawford, Journal American Chem. S. 88(1966) 3963–69.
R. J. Crawford, Journal American Chemical Society 88(1966), 3959–63.
E. L. Buhle et al., Journal American Chemical Society, 65(1943), 29–32.
A. Luttringhaus et al., Chem. Ber. 92 (1959), 1756.

Primary Examiner—Alan L. Rotman
Assistant Examiner—Kurt G. Briscoe
Attorney, Agent, or Firm—Keil & Weinkauf

[57] ABSTRACT

1-Pyrazolines are prepared by oxidation of a 1,3-diamine with sodium hypochlorite and a peroxide in aqueous solution.

2 Claims, No Drawings

PREPARATION OF 1-PYRAZOLINES

The present invention relates to an improved process for the preparation of 1-pyrazolines by oxidation of 1,3-diaminopropanes, the process being suitable for use on an industrial scale.

There is a need for an economical method of preparing 1-pyrazolines as intermediates for 2-pyrazolines, which are useful building blocks for heterocycles in the crop protection and pharmaceutical sectors. The raw material base for the synthesis of 1-pyrazolines is technically and economically more advantageous than that for the known direct syntheses of 2-pyrazolines.

To date, 1-pyrazolines have been obtainable only with difficulty and via reactions which give low yields of well below 30% (A. Weissberger (Editor), The Chemistry of Heterocyclic Compounds, Interscience Publishers, New York-London-Sydney 1967, Vol. 22, L.C. Behr, R. Fuser, C. H. Jarboe, Pyrazoles, Pyrazolines, Pyrazolidines etc., 177–208; R. J. Crawford, A. Mishra and R. J. Dummel, J. Amer. Chem. Soc. 88 (1966), 3959). They are thermodynamically less stable than the corresponding 2-pyrazolines (A. Weissberger, loc. cit.) and decompose readily into nitrogen and cyclopropanes (A. Weissberger, loc. cit.; R. J. Crawford and A. Mishra, J. Amer. Chem. Soc. 88 (1966), 3963).

The direct synthesis of the thermodynamically more stable 2-pyrazoline from an acrolein and a hydrazine (German Patent Application No. P 34 15 385.3) is too expensive for industrial purposes.

The synthesis of pyrazolidine by reacting a diaminopropane with sodium hypochlorite at below 0° C. is described in the literature (A. Luttringhaus, J. Jander and R. Schneider, Chem. Ber. 92 (1959), 1756). The pyrazolidine was not isolated as such but was reacted with benzenesulfonyl chloride to give a derivative in a yield of 33%.

Pyrazolidine prepared from 1,3-dibromopropane and hydrazine was dehydrogenated to 1-pyrazoline (R. J. Crawford, A. Mishra and R. J. Dummel, J. Amer. Chem. Soc. 88 (1966), 3959). The process is unsuitable for industrial purposes.

During the syntheses of pyrazolines and pyrazolidines from diamines, a large number of secondary reactions and side reactions take place when oxidative conditions are employed. Dimers have been observed (E. L. Buhle, A. M. Moore, F. Y. Wiselogle, J. Amer. Chem. Soc. 65 (1943), 29). All of the experiments described in the literature cited have been carried out only on a laboratory scale using very small amounts.

The reaction of amines with chlorine-containing compounds under oxidative conditions can lead to explosion of the reaction mixture (formation of extremely unstable $NCl_3$; textbooks of inorganic chemistry, eg. A. F. Hollemann and E. Wiberg, Lehrbuch der anorgan. Chemie, W. de Gruyter Verlag, Berlin 1971, 80th edition, page 349). This fact has acted as a deterrent to further investigations, especially on a larger scale.

It is an object of the present invention to provide a process for the preparation of 1-pyrazolines which is safe to carry out and can be used industrially.

We have found that this object is achieved by a process for the preparation of a 1-pyrazoline by oxidation of a 1,3-diaminopropane of the formula II

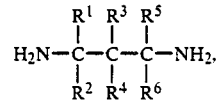

where $R^1$, $R^2$, $R^3$, $R^4$, $R^5$ and $R^6$ independently of one another are each hydrogen or alkyl of 1 to 3 carbon atoms, or two of the stated radicals which are bonded to the same carbon atom or to two adjacent carbon atoms together form an alkylene radical of 3 to 5 carbon atoms, in aqueous solution, wherein a 10–30, preferably 15–25, % strength solution of the diamine is initially taken, an aqueous solution of potassium hypochlorite or, preferably, sodium hypochlorite containing from 5 to 22, preferably from 15 to 19, % by weight of $OCl^-$ ions and a 20–50, preferably 40–50, % strength by weight aqueous solution of an oxidizing agent of the formula III $$R^3-O-O-H \qquad \text{III}$$

where $R^3$ is preferably hydrogen but may furthermore be alkyl of 1 to 5 carbon atoms or an aliphatic acyl radical of 2 to 5 carbon atoms, are run in simultaneously and slowly, in a molar ratio of hypochlorite to III of from 0.5 to 1.5, preferably from 0.9 to 1.1, while stirring, and care is taken to ensure that the reaction temperature does not exceed 60° C., preferably 30° C., as soon as possible after complete conversion of the diamine the resulting pyrazoline is extracted at room temperature with a hydrophobic organic solvent which dissolves pyrazoline, and is distilled under reduced pressure at below 100° C., preferably below 50° C. This procedure gives yields of 1-pyrazoline of about 90% or higher. The process has been carried out continuously without incidents (eg. explosions).

Instead of water as the reaction medium, it is also possible in principle to use an aqueous alcoholic mixture, although this is of no advantage.

The diamine solution is initially taken so that it does not come into contact with a large excess of oxidizing agent, which may result in decomposition. For the same reason, the reaction temperature must be controlled. The hypochlorite solution and the peroxide solution are run in separately or may be mixed with one another directly before addition. The hypochlorite is used in the form of a commercially available aqueous solution, as is the peroxide solution. Peroxide solutions having concentrations higher than 50% are not available commercially, and concentrations substantially lower than 20% would lead to unnecessary dilution of the reacton mixture. Suitable water-soluble peroxides include tert.-butyl hydroperoxide, peracetic acid and its homologs and, preferably, hydrogen peroxide.

The rate at which the oxidation solutions are fed in is determined by the reaction rate, enrichment of the oxidizing agent in the reaction space being avoided in this way. Both the hypochlorite concentration and the concentration of the oxidizing agent in the reaction mixture are kept below 5, preferably below 3, % by weight.

The reaction is advantageously monitored by gas chromatography and/or nuclear resonance spectroscopy. When conversion of the diaminopropane is complete, it is important for the feed of the two solutions of the oxidizing agents to be terminated immediately and the desired product to be isolated rapidly from the reaction mixture. The reaction time under the stated conditions is advantageously determined by a preliminary experiment. Isolation is effected by extraction with a hydrophobic solvent which readily dissolves the 1-pyrazoline and whose boiling point is well below or above that of the 1-pyrazoline, in order to facilitate separation by distillation. Examples of such solvents are aromatic and araliphatic hydrocarbons, halohydrocarbons, hydrophobic heterocycles, and N-butylbenzenesulfonamide. Quinoline and methylene chloride are preferred, the former remaining behind as a bottom product in the separation by distillation, and the latter distilling over.

Because of the solubilizing effect of the 1-pyrazoline, the extract also contains water. Working up is carried out by distillation under very greatly reduced pressure, ie. at very low temperatures, advantageously using a Sambay evaporator in order to expose the desired product to as little heat as possible.

This procedure gives an aqueous solution of the 1-pyrazoline. The water can in principle be separated off by distillation (over about 100 trays). However, this is neither necessary nor advisable for practical purposes since the stability of the 1-pyrazoline decreases with increasing concentration. As a rule, there is no advantage in increasing the concentration of 1-pyrazoline in water to above 40–50% by weight. Aqueous solutions are only stable if they are free of salts and of peroxides. It is for this reason that extraction must be carried out rapidly after the reaction.

Using the procedure described, it is possible to prepare not only 1-pyrazoline itself but, for example, also the following derivatives: 4,4-dimethyl-1-pyrazoline (from neopentanediamine) and bicyclo[3.3.0]-1,2-diaza-3,3a,4,5-6,6a-hexahydropentalene IV (from 2-aminomethylcyclopentylamine)

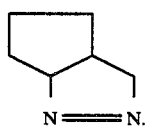

IV

The amino groups must be primary ones but need not be bonded to a primary carbon atom. However, the carbon atom which carries the amino group must not have bulky radicals which may prevent cyclization.

EXAMPLE 1

200 g of diaminopropane in 1000 ml of water were initially taken in a 6 l flask which was equipped with a condenser and a stirrer and to which two dropping funnels were attached. 750 ml of 50% strength $H_2O_2$ in water and 3000 ml of an aqueous NaOCl solution (18% by weight of hypochlorite ions) were simultaneously added dropwise in the course of 2.5 hours. The temperature in the flask remained below 50° C. The reaction was complete when all diaminopropane had been converted, this being detected by gas chromatography. Analysis of the reaction mixture gave a yield of 95% (quantitative GC and NMR). The mixture was immediately extracted continuously with quinoline at room temperature into two mixer-settler stages, the residence time being 1 hour and the ratio of quinoline to reaction mixture being 1:1). During this procedure, water dissolved in the quinoline. A Sambay evaporator operated continuously at room temperature and under 1.8 mbar was used, and water and 1-pyrazoline were removed from the quinoline and collected in a brine-cooled receiver. The 1-pyrazoline was obtained in the form of a 20% strength solution in water. The water and 1-pyrazoline were separated in a column having a large number of separating stages. The total yield of 1-pyrazoline was 70%. 1-Pyrazoline in aqueous solution can be isomerized to 2-pyrazoline in 90% yield, preferably under slightly alkaline conditions. The batchwise part of the experiment has been carried out about 30 times by different people. No explosions or unstable states occurred, and the system could be controlled safely.

EXAMPLE 2

300 g of diaminopropane in a mixture of 800 ml of water and 200 ml of methanol were initially taken in an apparatus similar to that described in Example 1 but with a 15 l vessel. 2500 ml of 30% strength $H_2O_2$ in water and 6000 ml of an aqueous NaOCl solution (12% by weight of hypochlorite ions) were simultaneously added dropwise in the course of 3 hours. The temperature in the flask remained below 40° C. Analysis of the reaction mixture (GC and NMR) gave a yield of 88%. The mixture was immediately extracted continuously with methylene chloride at room temperature into two mixer-settler stages, the residence time being 80 minutes and the ratio of methylene chloride to reaction mixture being 1:2. In this case too, water dissolved in the methylene chloride. A Sambay evaporator operated at 41° C. and under atmospheric or slightly reduced pressure was used, and the methylene chloride was stripped off. The 1-pyrazoline and water remained as a bottom product (about 30% strength solution). The total yield of 1-pyrazoline was 60%.

EXAMPLE 3

The same molar amount of 2-aminomethylcyclopentylamine was employed in a procedure similar to that described in Example 1. The reacted mixture contained bicyclo[3.3.0]1,2-diaza-3,3a,4,5,6,6a-hexahydropentalene, the yield being 80%.

EXAMPLE 4

Neopentanediamine was employed in a procedure similar to that described in Example 1. The reacted mixture contained 4,4-dimethyl-1-pyrazoline, the yield being 90%. Working up as described in Example 1 gave a total yield of 65%.

COMPARATIVE EXPERIMENT 1

(using 1,4-diaminobutane instead of 1,3-diaminopropane)

Diaminobutane was used in a procedure similar to that described in Example 1. The gas chromatogram of the reaction mixture showed a broad spectrum comprising different compounds. It was not possible to isolate a diazaheterocycle during the working up procedure.

COMPARATIVE EXPERIMENT 2

(using only NaOCl)

50 g (0.7 mole) of diaminopropane in 250 ml of water were reacted with 1350 ml of an aqueous NaOCl solution containing 80% by weight of $OCl^-$ (4.7 moles) by a procedure similar to that described in Example 1. The yield of 1-pyrazoline in the reacted mixture was 40%.

COMPARATIVE EXPERIMENT 3

(using only $H_2O_2$)

200 g (2.8 moles) of diaminopropane in 1000 ml of $H_2O$ were reacted with 1200 ml of 50% strength (about 17 moles) of aqueous $H_2O_2$ solution by a procedure similar to that described in Example 1. The yield of 1-pyrazoline in the reacted mixture was 35%.

We claim:

1. A process for the preparation of a 1-pyrazoline of the formula I

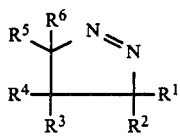

by oxidation of a 1,3-diaminopropane of the formula II in a reaction vessel

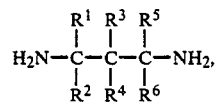

where $R^1$, $R^2$, $R^3$, $R^4$, $R^5$ and $R^6$ independently of one another are each hydrogen or alkyl of 1 to 3 carbon atoms, or two of the stated radicals which are bonded to the same carbon atom or to two adjacent carbon atoms together form an alkylene radical of 3 to 5 carbon atoms, in aqueous solution, which process comprises: simultaneously passing into said vessel a 10–30% strength solution of the diamine, an aqueous solution of hypochlorite containing from 5 to 22% by weight of hypochlorite ions and a 20–50% strength by weight aqueous solution of an oxidizing agent of the formula III

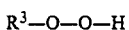

where $R^3$ is hydrogen, alkyl of 1 to 5 carbon atoms or an aliphatic acyl radical of 2 to 5 carbon atoms, in a molar ratio of hypochlorite to III of from 0.5:1 to 1.5:1, while stirring, and care is taken to ensure that the reaction temperature does not exceed 60° C., and as soon as possible after complete conversion of the diamine the resulting pyrazoline is extracted at room temperature with a hydrophobic organic solvent which dissolves pyrazoline, and is distilled under reduced pressure at below 100° C.

2. The process of claim 1, wherein the aqueous sodium hypochlorite solution contains from 15 to 19% by weight of hypochlorite ions and the oxidizing agent is a 40-50% strength aqueous hydrogen peroxide solution, the solution of hyprochlorite ions and the solution of hydrogen peroxide being passed into the vessel at a rate that is sufficiently slow so that the concentration of hypochlorite and of oxidizing agent III in the reaction medium does not exceed 5% by weight in each case.

* * * * *